United States Patent [19]

Peck

[11] Patent Number: 5,575,296
[45] Date of Patent: Nov. 19, 1996

[54] FINGER PUNCTURE PROTECTOR

[76] Inventor: Edward F. Peck, 4908 Edinborough Rd., Greensboro, N.C. 27401

[21] Appl. No.: 417,814

[22] Filed: Apr. 6, 1995

Related U.S. Application Data

[63] Continuation of Ser. No. 149,055, Nov. 8, 1993, Pat. No. 5,415,184, which is a continuation of Ser. No. 914,803, Jul. 16, 1992, abandoned.

[51] Int. Cl.⁶ .................................................. A61D 19/00
[52] U.S. Cl. ................................................. 128/880; 2/163
[58] Field of Search ....................................... 128/878, 879, 128/880; 2/20, 21, 16, 163, 164, 167; 602/22; D7/631, 632; D19/34

[56] References Cited

U.S. PATENT DOCUMENTS

| | | |
|---|---|---|
| 129,392 | 7/1872 | Budington . |
| 135,305 | 1/1873 | Ackley et al. . |
| 136,640 | 3/1873 | Bond . |
| 203,978 | 5/1878 | Woods . |
| 207,708 | 9/1878 | Boyer . |
| D. 230,915 | 3/1974 | Fowler . |
| 293,831 | 2/1884 | Wickers . |
| 310,108 | 12/1884 | Winzenried . |
| D. 332,726 | 1/1993 | Goodman . |
| 408,052 | 7/1889 | Stoll . |
| 460,104 | 9/1891 | Barrett . |
| 540,975 | 6/1895 | Grimes . |
| 549,229 | 11/1895 | Connelly . |
| 594,499 | 11/1897 | Suit . |
| 622,386 | 4/1899 | Perry . |
| 666,666 | 1/1901 | Hackett . |
| 681,054 | 8/1901 | Hawley . |
| 760,339 | 5/1904 | Marsh . |
| 843,819 | 2/1907 | Huntley . |
| 911,823 | 2/1909 | Krieger . |
| 945,818 | 1/1910 | Sprague . |
| 971,093 | 9/1910 | Ward . |
| 1,160,522 | 11/1915 | Morris . |
| 1,220,007 | 3/1917 | Rowley . |
| 1,257,846 | 2/1918 | Gregory . |
| 1,268,103 | 6/1918 | Fleming . |
| 1,408,070 | 2/1922 | Boehringer . |
| 1,664,542 | 4/1928 | Douglass . |
| 1,761,356 | 6/1930 | McNamara . |
| 1,854,047 | 4/1932 | Kurtz, Jr. . |
| 2,075,413 | 3/1937 | Welker . |
| 2,118,360 | 5/1938 | Sager . |
| 2,225,571 | 12/1940 | Smith . |
| 2,424,318 | 5/1941 | Mosier . |
| 2,460,155 | 1/1949 | Talarico . |
| 2,535,114 | 12/1950 | Acton . |
| 3,074,399 | 1/1963 | Bitting . |
| 3,228,033 | 1/1966 | Ames . |
| 4,460,113 | 7/1984 | Nicklous . |
| 4,507,804 | 4/1985 | Consigny . |
| 4,541,749 | 9/1985 | McCoy . |
| 4,638,511 | 1/1987 | Haack . |
| 4,825,470 | 5/1989 | Horio . |
| 4,858,245 | 8/1989 | Sullivan et al. . |
| 4,864,661 | 9/1989 | Gimbel . |
| 4,873,998 | 10/1989 | Joyner . |
| 4,901,372 | 2/1990 | Pierce . |
| 4,915,229 | 4/1990 | Yamada . |
| 4,942,626 | 7/1990 | Stern et al. . |
| 4,985,038 | 1/1991 | Lyell . |
| 5,016,286 | 5/1991 | Henriksen . |
| 5,070,543 | 12/1991 | Beck . |

FOREIGN PATENT DOCUMENTS

| | | |
|---|---|---|
| 963141 | 5/1957 | Germany . |
| 357255 | 6/1930 | United Kingdom . |

OTHER PUBLICATIONS

*Gift & Tableware Reporter* Aug. 1975 Vincent Lippe p. 21.

*Primary Examiner*—Sam Rimell

[57] ABSTRACT

A finger protector for protecting the fingers of health care workers from inadvertent needle stabs during arterial blood gas sampling and intravenous and intra-arterial catheter insertion includes a housing to be received on the fingers. The housing is fabricated from a puncture resistant, and preferably rigid and transparent material, and includes apertures on a lower Surface for permitting tactile contact of the finger tip(s) with the skin surface for facilitating palpation of the body surface.

13 Claims, 3 Drawing Sheets

FINGER PUNCTURE PROTECTOR

This is a continuation of Ser. No. 08/149,055 filed Nov. 8, 1993, now U.S. Pat. No. 5,415,184, which was a continuation of Ser. No. 07/914,803, filed Jul. 16, 1992, now abandoned.

BACKGROUND OF THE INVENTION

1. Field of the Invention

The present invention relates to a protective device which may be worn by a health care worker to protect the fingers from inadvertent punctures by a needle.

2. Background of the Art

Health care workers require protection from needle punctures in the health care environment. Puncture protection for the fingers is especially needed during arterial blood gas sampling, intravenous catheter insertion, and like procedures, wherein there is a likelihood of the hand opposite to that holding the needle getting punctured inadvertently.

For example, in procedures for taking arterial blood gas samples, or other intravenous therapy, the practitioner is required to palpate the artery using the finger tips of the index and middle fingers in order to prevent the artery, or vein from rolling during insertion of the needle. This requires maximum tactility of the finger tip area of the index and middle fingers. The needle is inserted into the patient ¼" or less from the index finger of the practitioner. Once inserted into the patient's body, the needle becomes contaminated with the patient's body fluids. With close proximity of the needle to the index finger of the practitioner there is a possibility that the finger will be accidentally punctured with a contaminated needle, especially since the patient may have a tendency to pull back or move the limb in response to insertion of the needle.

One means of protection available to the health care practitioner is the use of surgical gloves made from rubber or latex, or similar material. While latex or rubber gloves allow for the tactility required for palpation, such gloves typically do not afford adequate protection from needle stabs. Consequently, additional protection is required.

U.S. Pat. No. 4,942,626 to Stem et at. discloses a glove for use by medical personnel which is adapted to help prevent accidental needle stabs. The glove comprises a two-ply construction of leather and includes finger tip holes on the index and middle finger stalls for allowing direct contact of the finger tips with the patient's limb for tactility.

U.S. Pat. No. 4,864,661 to Gimbel discloses a surgical glove having puncture resistant areas to protect the health care practitioner from punctures by needles, scalpels, and other sharp or pointed instruments. The puncture resistant areas includes layers of woven puncture resistant materials such as fiberglass fabric, aramid fiber, ballistic nylon, high modulus polyethylene, or panels of hard ceramics such as boron carbide or silicon carbide.

U.S. Pat. No. 4,901,372 to Pierce discloses a barrier surgical glove, cot, or hand coveting having a tri-laminar construction with continuous inner and outer barrier layers and a central foam layer.

U.S. Pat. No. 549,229 to Connelly discloses a finger shield of puncture resistant material to protect the user from needle pricks during sewing. The finger shield is placed over the tip of the index finger, and has an aperture to expose a portion of the finger tip to permit the fabric to be held more securely between the index finger and the thumb.

Although various types of finger puncture protectors are known in the art, there yet remains a need for a finger puncture protector which is easy to use inexpensive, practical, and effective for preventing needle pricks by contaminated needles during intravenous and intra-arterial catheter insertion and arterial blood gas sampling.

SUMMARY

A finger protector for protecting the fingers of health care workers from inadvertent punctures by needles is provided herein. The finger puncture protector comprises a housing fabricated from puncture resistant material and includes an upper surface; a lower surface having aperture means for permitting tactile contact of at least one finger through said aperture means; at least one side potion joining the upper and lower surfaces and reception means, such as an interior chamber and proximal opening, for receiving at least two fingers of a user's hand-within said housing.

The puncture resistant material is preferably rigid and transparent, and may be a polymer such a polycarbonate or acrylic. The housing is preferably of unitary construction. The material may optionally be tinted as long as the outline of the user's hand can be seen.

In an embodiment useful on either the left and right hand, the protector includes right and left side portions and the aperture means comprises first and second apertures, the first aperture being located adjacent one of the left and right sides, and the second aperture being located adjacent the other of the first and second sides. In this embodiment, the first aperture is located so as to permit tactile contact therethrough of a left hand index finger, and the second aperture is located so as to permit tactile contact therethrough of a fight hand index finger.

BRIEF DESCRIPTION OF THE DRAWINGS

Preferred embodiments of the invention are described hereinbelow wherein.

DETAILED DESCRIPTION OF PREFERRED EMBODIMENTS

As used in the following discussion of the finger protector of this invention, references to the proximal end of the protector refer to the end closest to the user. The distal end of the protector refers to the end furthest from the user, i.e. the end at which the finger tips are located. When reference is made in the discussion to the left or right side of the protector, the side is determined by viewing the protector from the proximal end thereof with the top Side up.

The finger protector of the present invention as described herein with reference to any of the disclosed embodiments is preferably of unitary construction and fabricated from any material resistant to puncture. In preferred embodiments, the finger protector is fabricated from transparent and rigid material such as polymeric resins including, but not limited to, polycarbonates, acrylics, and the like. When inserted into the finger protector, the fingers are in contiguity, i.e., there are no separate stalls or compartments for each finger such as provided by a glove. Rather, a single compartment or chamber is provided for holding all of the received fingers. The finger protector will be used in conjunction with rubber or latex surgical gloves, i.e., the health care worker will first put on a surgical glove-and then wear the finger protector over the glove.

Figure 2:
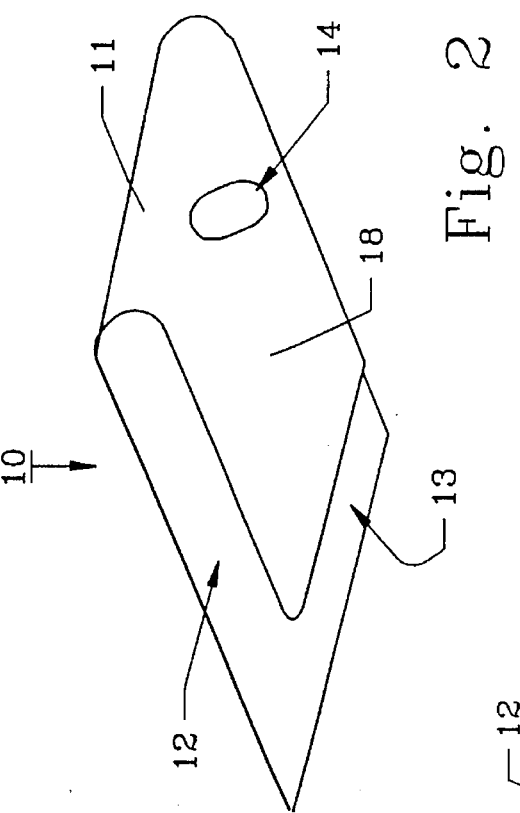
FIGS. 1, 2, and 3 are, respectively, a perspective view from above, a perspective view from below, and a bottom view, showing an embodiment of the finger protector of the present invention.
Figure 3:
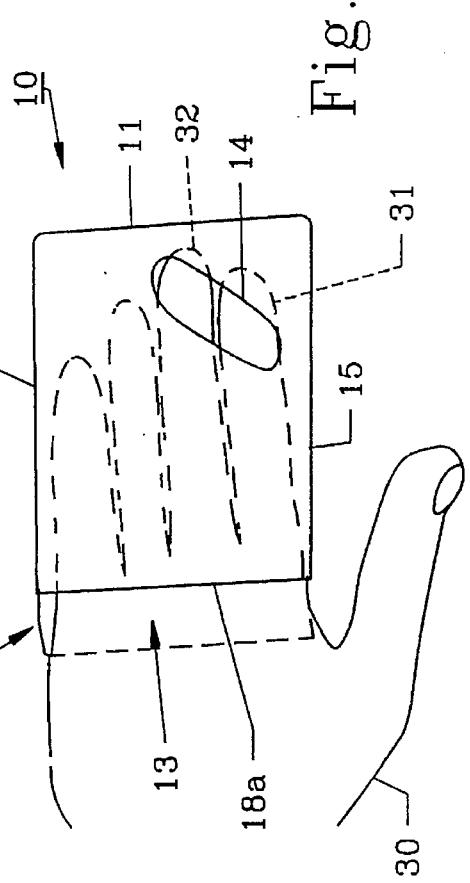
Figure 1:
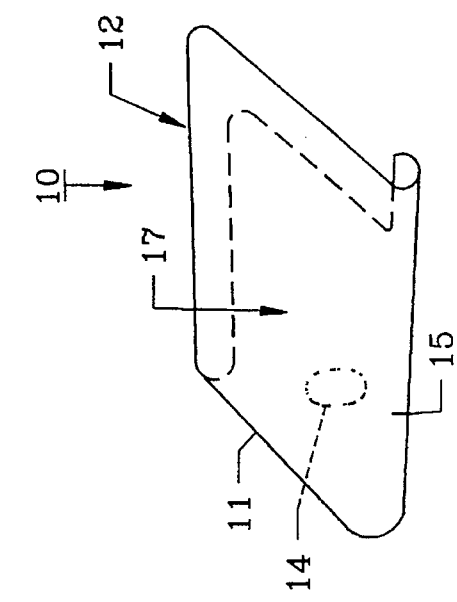

Referring to FIGS. 1, 2 and 3, a first embodiment of the finger protector 10 includes a top surface 17, a bottom surface 18, a distal end 11, a closed side 15, and open side 12 and an open proximal end 13. The finger protector 10 illustrated in FIGS. 1, 2 and 3, is adapted for coveting the fingers of the user's fight hand 30. One skilled in the art can readily construct a left hand embodiment of the finger protector 10, which is also considered to be within the scope of this invention. At least two fingers, and preferably four fingers exclusive of the thumb are held in contiguity within the interior of the finger protector 10. The index and middle finger are the fingers customarily used for palpation and are intended to be inserted within the finger protector 10. Thus, closed side 15 extends along the left side of the finger protector 10 so as to be in proximity to the index finger of the fight hand, and open side 12 is located along the right side. The open side 12 allows the fingers to be inserted into the finger protector 10 laterally therethrough. In a finger protector 10 adapted for use on the health care worker's left hand the closed side 15 will be located along the right side of the protector 10 and the open side 12 will be located along the left side thereof.

The finger puncture protector 10 further includes aperture 14 in the bottom surface 18 to permit tactile contact between the tips of the index and middle fingers 31 and 32, respectively, of hand 30, for palpating the body surface.

The finger protector 10 can also include a portion 16 of the top surface 17 which extends proximally or rearward beyond the proximal edge 18a of the bottom surface 18. The extra extension of portion 16 provides protection for the-knuckles over which portion 16 extends.

The unique construction of the finger protector 10 affords protection from needle stabs, permits tactile contact for palpation, and enables the finger protector 10 to be fabricated from a relatively inexpensive material such that the finger protector 10 may be disposable after a single use, or optionally used again after sterilization.

Figure 4:
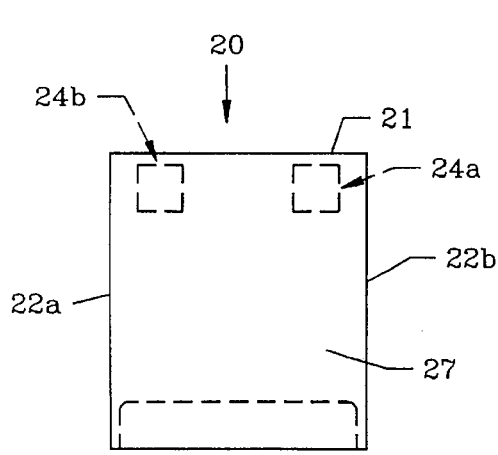
FIGS. 4, 5 and 6 are, respectively, top view, bottom view, and perspective view from below, showing an alternative embodiment of the finger protector of the present invention.
Figure 5:
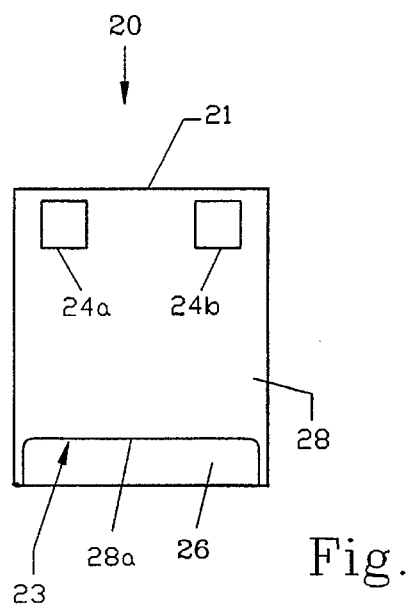
Figure 6:
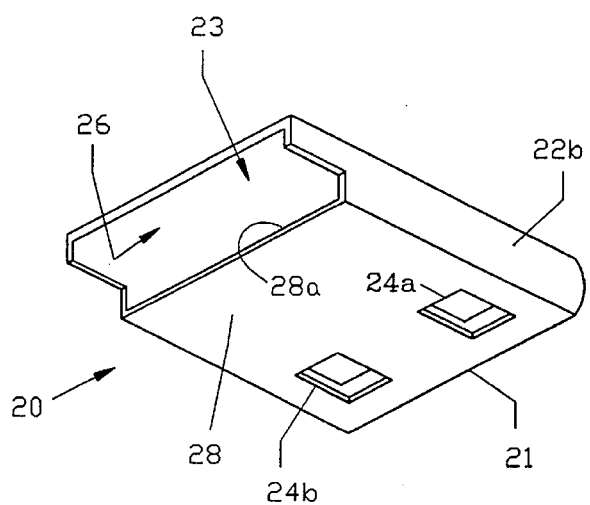

Referring now to FIGS. 4, 5 and 6, an alternative embodiment 20 of the finger protector is illustrated. Finger protector 20 includes a distal end 21; left and right walls 22a and 22b, respectively; a top surface 27; a bottom surface 28 and a proximal opening 23. Finger protector 10 can also include a portion 26 of the top surface 27, which extends proximally or rearward beyond proximal edge 28a of the lower surface 28. The extra extension of portion 26 provides protection for the knuckles over which portion 26 extends when finger protector 20 is worn on the user's hand.

The finger puncture protector 20 preferably further includes at least two apertures 24a and 24b in the bottom surface 28 for permitting tactile contact of at least the index finger with the body surface to be palpated.

Unlike the previously described embodiment, the finger protector 20 may be worn individually on both the left and the fight hand. Apertures 24a and 24b are located such that, if the fight hand is inserted into finger protector 20, at least the index finger of the right hand will be positioned over aperture 24b, for tactile contact therethrough. If the left hand of the user is inserted into finger protector 20, at least the index finger of the left hand will be positioned over aperture 24a for tactile contact therethrough.

The apertures of both embodiment 10 and 20, described above, may be of any shape and size suitable for the purpose of permitting tactile contact for palpation. Thus, the shape of the apertures may be rounded, square, rectangular, oval, and the like and may be oriented at an angle to the longitudinal axis of the finger protector, as shown in FIG. 3. The aperture may be sufficiently large to allow tactile contact by two or more fingers, such as for example the index and middle fingers of the hand.

Moreover, while embodiment 20 is shown as having two apertures, a single aperture extending laterally across the bottom surface 28 would also be effective for providing tactile access and for permitting use of the finger protector 20 on both the left and fight hands. However, a single aperture extending across the finger protector might also provide more open space and less security. Hence, the minimum amount of aperture area required for palpation is desirable.

Figure 7:
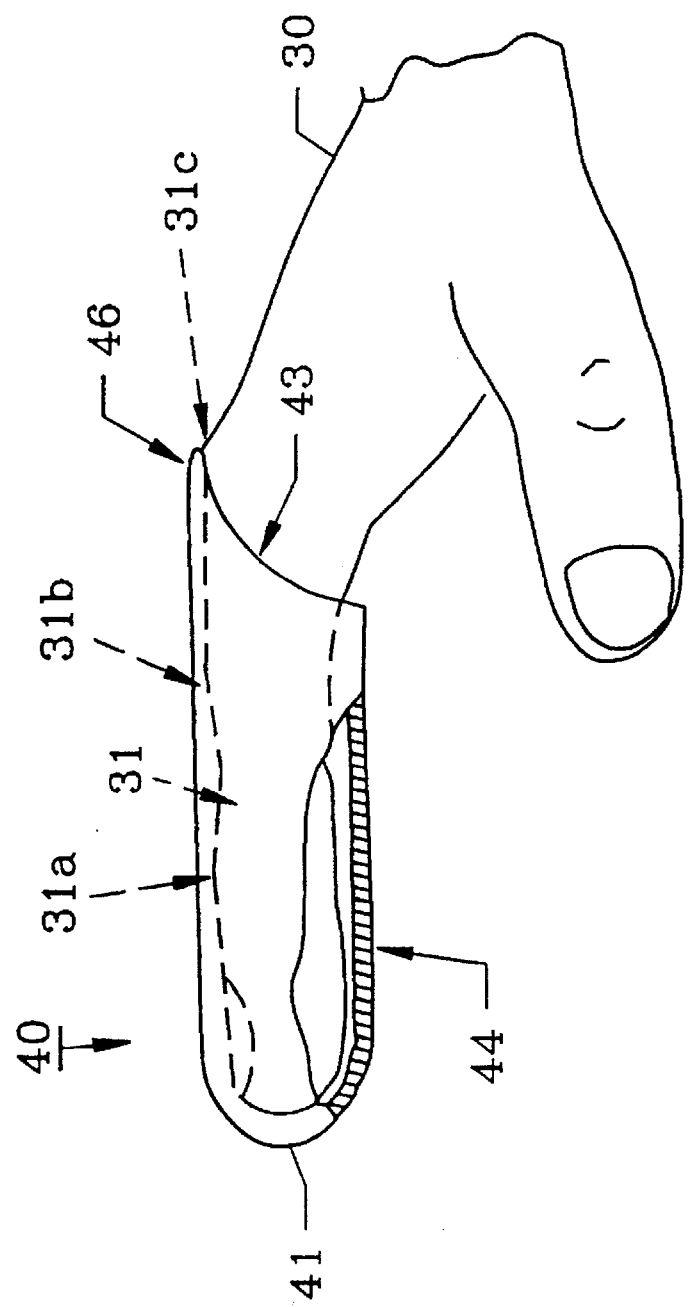
FIG. 7 is a partly sectional side view of another embodiment of the finger protector of the present-invention.

Referring to FIG. 7, an alternative embodiment 46 of the finger protector is shown. Finger protector 40 comprises a housing of rigid, puncture-resistant material for receiving a single finger 31 of the user's hand to cover a substantial portion of the finger on all sides. As described above, the material of fabrication can be a polycarbonate or acrylic plastic and is preferably transparent.

Finger protector 40 has a closed distal end 41, an opening 43 in the proximal end to permit entry of single finger therein, a proximal extension 46 to cover the knuckle 31c, i.e. the joint connecting the finger to the rest of the hand, and an aperture 44 for permitting tactile contact of the finger with objects outside the housing.

The housing is of sufficient length to enclose the first and second joints 31a and 31b, respectively, of finger 31, and is preferably of unitary single-piece construction.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended thereto.

What is claimed is:

1. A finger protector for protecting a human hand having fingers with tips, tip pads, and knuckles from needle punctures, said protector comprising: a rigid needle puncture resistant rectangular box-like housing, said housing having a planar bottom, a top, a first continuous side wall, a second continuous side wall, and a distal closed end, said top spaced from and secured to said planar bottom by continuous and closed attachment of said distal closed end and said first and second continuous side walls, said distal closed end, said first and second continuous side walls, said top, and said bottom defining a closed container having a proximal opening for reception of at least one of the fingers, so the finger tip pad of the contained finger within said housing container is adjacent said distal closed end, said bottom having a length from said distal closed end to said proximal opening less than the length of the finger, said bottom having a lower surface, and said bottom defining an aperture contiguous said distal closed end within said closed container, said aperture sized to only expose the finger tip pad, said aperture contiguous said distal closed end to allow the finger tip pad to extend below said bottom surface to allow tactile feeling outside the container housing when the finger is completely inserted into said closed container.

2. The finger protector of claim 1 wherein the distance from said first continuous side wall to said second continuous side wall is sufficient to contain two fingers within said closed container.

3. The finger protector of claim 1 wherein the distance from said first continuous side wall to said second continuous side wall is sufficient to contain three fingers within said closed container.

4. The finger protector of claim 1 wherein the distance from said first continuous side wall to said second continuous side wall is sufficient to contain four fingers within said closed container.

5. The finger protector of claim 1 wherein said first and second continuous side walls are planar and normal to said top and said bottom.

6. The finger protector of claim 1 wherein said top comprises a proximal extension which covers the knuckle of the finger contained within said closed container.

7. The finger protector of claim 1 wherein said aperture defined by said bottom is square with side lengths less than the length and width of the finger tip pad contained adjacent said distal closed end.

8. A finger protector for protecting a human hand having adjacent fingers with tips, tip pads, and knuckles from needle punctures, said protector comprising: a rigid needle puncture resistant housing, said housing having a planar bottom, a planar top, a closed end and a closed side, said planar top spaced from and secured to said planar bottom by continuous attachment of said closed end and said closed side, said closed end and said closed side normal to said planar bottom and said planar top, wherein said closed end, said closed side, said planar bottom and said planar top define a closed container for receiving a finger adjacent said closed side with the finger tip of the finger adjacent said closed end, said bottom having a length from said closed end along said closed side less than the length of the finger adjacent said closed side, said bottom having a lower surface, said bottom defining an aperture sized to only expose the finger tip pad, contiguous said closed end within said closed container, said aperture of sufficient dimension to allow the finger tip of the finger adjacent said closed side to extend below said lower surface of said bottom when the finger is completely inserted into said closed container.

9. The finger protector of claim 8 wherein said planar top comprises a proximal extension.

10. The finger protector of claim 8 wherein the width of said planar top and said planar bottom is dimensioned to enclose two adjacent fingers.

11. The finger protector of claim 8 wherein the width of said planar top and said planar bottom is dimensioned to enclose three adjacent fingers.

12. The finger protector of claim 8 wherein the width of said planar top and said planar bottom is dimensioned to enclose four adjacent fingers.

13. The finger protector of claim 10 wherein said aperture proximate said closed end is dimensioned to allow the finger tip pads of the two enclosed adjacent fingers to extend below said lower surface of said bottom.

* * * * *